(12) United States Patent
Choi et al.

(10) Patent No.: US 9,072,593 B2
(45) Date of Patent: Jul. 7, 2015

(54) ARTIFICIAL NEPHRON DEVICE

(75) Inventors: Bum Kyoo Choi, Seoul (KR); Seung Joon Lee, Incheon (KR)

(73) Assignee: INDUSTRY-UNIVERSITY COOPERATION FOUNDATION SOGANG UNIVERSITY, Seoul (KR)

( * ) Notice: Subject to any disclaimer, the term of this patent is extended or adjusted under 35 U.S.C. 154(b) by 0 days.

(21) Appl. No.: 13/812,487

(22) PCT Filed: Dec. 24, 2010

(86) PCT No.: PCT/KR2010/009318
§ 371 (c)(1),
(2), (4) Date: Jan. 25, 2013

(87) PCT Pub. No.: WO2012/015124
PCT Pub. Date: Feb. 2, 2012

(65) Prior Publication Data
US 2013/0123936 A1     May 16, 2013

(30) Foreign Application Priority Data

Jul. 29, 2010    (KR) ........................ 10-2010-0073127

(51) Int. Cl.
*A61F 2/04* (2013.01)
*B01D 61/00* (2006.01)
*A61M 1/14* (2006.01)
*A61M 1/34* (2006.01)

(52) U.S. Cl.
CPC .. *A61F 2/04* (2013.01); *A61M 1/14* (2013.01); *A61M 1/34* (2013.01)

(58) Field of Classification Search
CPC .......... A61F 2/04; B01D 63/00; B01D 61/00; C02F 1/44

USPC ............ 623/23.65–23.66; 210/321.6–321.72, 210/500.21
See application file for complete search history.

(56) References Cited

FOREIGN PATENT DOCUMENTS

| JP | 05-176991 A | 7/1993 |
|---|---|---|
| JP | 2007-325679 | 12/2007 |
| KR | 10-0750511 B1 | 8/2007 |

OTHER PUBLICATIONS

E. Weinberg et al., "Concept and computational design for a bioartificial nephron-on-a-chip", The International Journal of Artificial Organs, Jun. 2008, pp. 508-514, vol. 31, No. 6.
Ye Gu et al., "Multilayered microfilter using a nanoporous PES membrane and applicable as the dialyzer of a wearable artificial kidney", Journal of Micromechanics and Microengineering, Jun. 2009, pp. 1-8, vol. 19, No. 6.

*Primary Examiner* — Yashita Sharma
(74) *Attorney, Agent, or Firm* — Rabin & Berdo, P.C.

(57) ABSTRACT

The present invention relates to an artificial nephron device. The artificial nephron device comprising a multi micro channel in which while blood containing waste and water are passing therethrough the waste is separated so as to purify the blood and the separated waste is concentrated into the water to be discharged, wherein the multi micro channel comprises a glomerulus micro channel simulating a Glomerulus, a tubule micro channel simulating a Tubule, and a Henle's loop micro channel simulating a Henle's loop. According to the present invention, the device can be made smaller and can be optimized, and an artificial kidney of high efficiency can be made by the series or parallel combination of the devices, so the demand for a portable artificial kidney and the domiciliary hemodialysis system can be increased and life quality of patients suffering from chronic renal insufficiency can be improved.

7 Claims, 4 Drawing Sheets

ARTIFICIAL NEPHRON DEVICE

FIELD OF THE INVENTION

The present invention relates to an artificial nephron device.

BACKGROUND ART

With the acceleration of aging phenomenon, the number of patients suffering from chronic renal insufficiency among whom age of fifties or more than the same is more than 80% are increasing and the related market size is highly increasing by more than 10% every year.

Looking at the current situation of domestic and foreign related technologies for patients suffering from chronic renal insufficiency, there is a hemodialysis device (i.e., an artificial kidney). This is used to treat the patient suffering from chronic renal insufficiency, and the treatment is performed three times per week and every treatment takes four to five hours. For the treatment using the hemodialysis device, an arteriovenous fistula operation should be performed previously. This is an operation to enlarge a blood vessel by connecting the neighboring artery and vein because it is impossible to use ordinary blood vessels of a patient for inserting a big injection needle thereinto. By connecting a hemodialysis device to the enlarged vein after an arteriovenous fistula operation, hemodialysis is performed.

In addition, a portable artificial kidney which can be worn to the body of a patient is being developed. However this has an advantage over the above-described hemodialysis device in that this allows the domiciliary treatment, it has a poor treatment efficiency because of a portable device, and domestic and foreign researches for developing a device with high efficiency are being made.

Recently, an atmosphere that a new approach for an artificial kidney to overcome the limitation of the conventional artificial kidney is prevalent.

DETAILED DESCRIPTION OF THE INVENTION

Technical Problem

The present invention has been made in an effort to provide an artificial nephron device which can be made smaller and can be optimized, and an artificial kidney of high efficiency can be made by the series or parallel combination of the devices, so the demand for a portable artificial kidney and the domiciliary hemodialysis system can be increased and life quality of patients suffering from chronic renal insufficiency can be improved.

Technical Solution

In an exemplary embodiment of the present invention, an artificial nephron device includes a multi micro channel in which while blood, which contains waste, and water are passing therethrough, the waste is separated so as to purify the blood and the separated waste is concentrated into the water to be discharged, wherein the multi micro channel includes a glomerulus micro channel simulating a Glomerulus, a tubule micro channel simulating a Tubule, and a Henle's loop micro channel simulating a Henle's loop.

The artificial nephron device according to another embodiment of the present invention may include: a blood purification passage including a blood inlet through which the blood is supplied, a blood outlet through which the blood purified while passing through the multi micro channel is discharged, and a blood passage which sequentially connects the blood inlet, the glomerulus micro channel, the tubule micro channel, the Henle's loop micro channel and the blood outlet; a water inlet flowing water into the glomerulus micro channel, the tubule micro channel and the Henle's loop micro channel; and a waste concentration passage including a waste outlet through which the waste having been concentrated into the water while passing through the multi micro channel is discharged, and a waste passage which sequentially connects the glomerulus micro channel, the tubule micro channel, the Henle's loop micro channel and the waste outlet.

The glomerulus micro channel may separate small molecule from the blood and may merge the same into the water and may remain large molecule to the blood, the large molecule may include hemoglobin, and the small molecule comprises glucose and urea.

The glomerulus micro channel may flow water thereinto and may use diffusion for the separation between the large molecule and the small molecule.

The tubule micro channel may separate the water containing the small molecule into the water containing the glucose and the water containing the urea.

Te tubule micro channel may flow water thereinto separately from the water containing the small molecule and may use diffusion and electro osmotic flow for the separation between the small molecules.

The Henle's loop micro channel may regulate the amounts of water, according to the osmotic pressure, respectively in the water containing the glucose, the water containing the urea, and the water which is flowed thereinto separately from the water containing the glucose and the water containing the urea, and may subsequently merge the water containing the glucose into the blood containing the remained hemoglobin to discharge as the purified blood, and may discharge the water containing the urea as the water containing the waste.

Advantageous Effects

According to the present invention, the device can be made smaller and can be optimized, and an artificial kidney of high efficiency can be made by the series or parallel combination of the devices, so the demand for a portable artificial kidney and the domiciliary hemodialysis system can be increased and life quality of patients suffering from chronic renal insufficiency can be improved.

DETAILED DESCRIPTION OF THE EMBODIMENTS

An embodiment of the present invention will be described in detail with reference to the accompanied drawings hereinafter.

Figure 1:
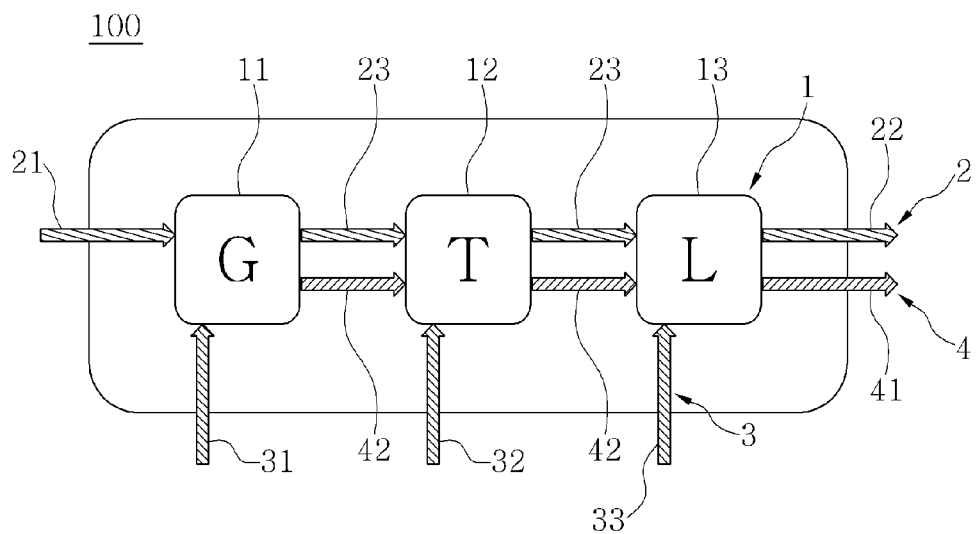
FIG. 1 is a block diagram of an artificial nephron device according to an embodiment of the present invention.

An artificial nephron device 100 according to an embodiment of the present invention relates to a device simulating a nephron (Glomerulus, Tubule, Henle's loop) of a human body which is composed of multi micro channels using principles of diffusion, electro osmotic flow and osmotic pressure, and referring to FIG. 1, includes a multi micro channel 1 in which if blood 200 including waste 300 and water 400 are flowed therethrough, the waste 300 is separated from the blood 200 so that the blood 200 is purified and the waste 300 is excreted by being concentrated into the water 400. That is, the blood 200 is purified through the multi micro channel 1, and the waste 300 is concentrated as urine to the water 400.

Referring to FIG. 1 to FIG. 4, the multi micro channel 1 includes a glomerulus micro channel (G) 11 simulating a Glomerulus, a tubule micro channel (T) 12 simulating a renal Tubule, and a Henle's loop micro channel (L) 13 simulating a Henle's loop.

Exemplarily, the glomerulus micro channel 11 may play a role of remaining hemoglobin 221 to the blood 200 and separating glucose 211 and urea 212 from the blood 200, among hemoglobin 221, glucose 211 and urea 212 which are contained in the blood 200 with the waste 300. In addition, the tubule micro channel 12 may play a role of separating glucose 211 and urea 212. In addition, Henle's loop micro channel 13 balances proportionably amounts of the water 400 respectively including glucose 211 and urea 212 according to an osmotic pressure and subsequently merges the water 400 having glucose 211 into the blood 200 to discharge as the purified blood 200 and excretes the water 400 including urea 212 as the water including the waste 400. The function of the multi micro channel 1 will be described with the description of function and effect of the artificial nephron device 100 later in more detail.

In addition, referring to FIG. 1, the artificial nephron device 100 according to an embodiment of the present invention may further include a blood purification passage 2, a water inlet 3 and a waste concentration passage 4.

Referring to FIG. 1, the blood purification passage 2 may include a blood inlet 21 through which the blood 200 is supplied, a blood outlet 22 through which the blood 200 purified while passing through the multi micro channel 1 is discharged, and a blood passage 23 which sequentially connects the blood inlet 21, the glomerulus micro channel 11, the tubule micro channel 12, the Henle's loop micro channel 13 and the blood outlet 22.

The water inlet 3 may flow water into the glomerulus micro channel 11, the tubule micro channel 12 and the Henle's loop micro channel 13. Exemplarily, referring to FIG. 1 to FIG. 4, the water inlet 3 may be provided for the respective micro channels 11, 12 and 13 so as to use diffusion, electroosmotic flow, osmotic pressure, and the like. That is, a glomerulus micro channel water inlet 31 may be provided to the glomerulus micro channel 11, a tubule micro channel water inlet 32 may be provided to the tubule micro channel 12 and a Henle's loop micro channel water inlet 33 may be provided to the Henle's loop micro channel 13. The water 400 without other components can be supplied through the respective water inlets 31, 32 and 33.

Further, the waste concentration passage 4 may include a waste outlet 41 through which the waste 300 having been concentrated into the water 400 while passing through the multi micro channel 1 is discharged, and a waste passage 42 which sequentially connects the glomerulus micro channel 11, the tubule micro channel 12, the Henle's loop micro channel 13 and the waste outlet 41. Here, the blood outlet 22 or the blood passage 23 may be connected to the waste outlet 41 or the waster passage 42. However, it may also be possible to be configured such that the components contained to the blood 200 or the water 400 can be exchanged within the respective micro channels 11, 12 and 13.

Hereinafter, function and effect of the artificial nephron device 100 will be described with respect to the lower construction of the multi micro channel 1.

First, function and effect of the glomerulus micro channel 11 will be described.

Figure 2:
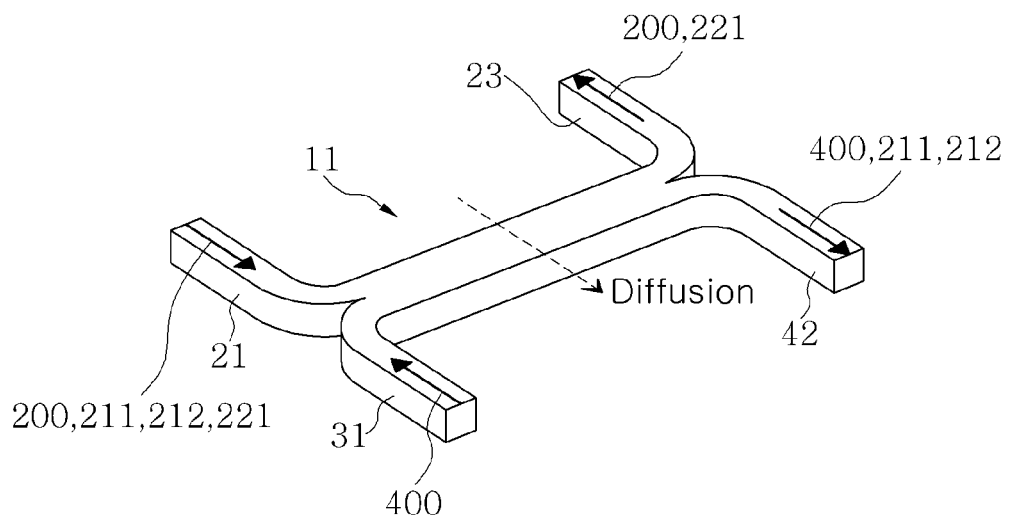
FIG. 2 is a conceptual diagram of a glomerulus micro channel.

Referring to FIG. 1 and FIG. 2, the glomerulus micro channel 11 may separate small molecule 210 from the blood 200 and may merge the same into the water 400 and may remain large molecule 220 to the blood 200. Here, the larger molecule 220 may include the hemoglobin 221, and the small molecule 210 may include the glucose 211 and the urea 212.

Further, the glomerulus micro channel 11 may flow the water 400 thereinto and may use diffusion for the separation between the large molecule 220 and the small molecule 210. Here, the diffusion means a phenomenon that particles of solution move by itself due to the difference of density or concentration to spread into liquid or gas from higher concentration (density) side to lower concentration (density) side. According to Graham's diffusion speed law, the diffusion speed is inversely proportional to square root of molecular weight (or density) under the same temperature and pressure, so it can be known that the diffusion speed becomes higher as the molecular weight and the density become smaller.

Exemplarily, referring to FIG. 1 and FIG. 2, if the blood 200 containing the hemoglobin 221, the glucose 211, the urea 212, or the like is flowed through the blood inlet 21 and the water 400 is supplied through the water inlet 31 to the glomerulus micro channel 11, the diffusion occurs so that the hemoglobin 221 which belongs to the large molecule 220 having much larger and heavier than the glucose 211 and the urea 212 remains in the blood 200 so as to discharge through the blood passage 23 and the glucose 211 and the urea 212 which belong to the small molecule 210 move to the water 400 which have lower concentration or density so as to be discharged through the waste passage 42 together with the water 400.

Subsequently, function and effect of the tubule micro channel 12 will be described.

Figure 3:
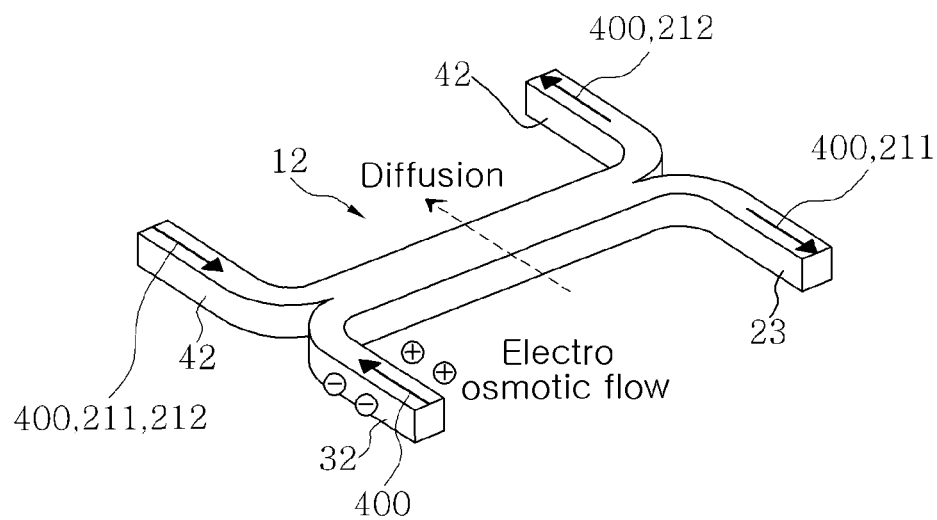
FIG. 3 is a conceptual diagram of a tubule micro channel.

Referring to FIG. 1 and FIG. 3, the tubule micro channel 12 may separate the water 400 containing the small molecule 210 into the water 400 containing the glucose 211 and the water 400 containing the urea 212. The glomerulus micro channel 11 performs the function of particle separation between the large molecule 220 and the small molecule 210, and the tubule micro channel 12 performs the function of particle separation between the small molecules 210.

In addition, the tubule micro channel 12 may flow the water 400 thereinto separately from the water 400 containing the small molecule 210 and may use diffusion and electro osmotic flow for the separation between the small molecules 120. Here, the electro osmotic flow means flow which is formed by the movement of the electrically charged particles by electrostatic attraction force in the electrical double layers just like the movement of a conveyor belt. The device for using the electro osmotic flow is not shown in the drawing.

Exemplarily, referring to FIG. 1 and FIG. 3, if the glucose 211 and the urea 212 which was discharged together with the water 400 through the waste passage 42 from the glomerulus micro channel 11 are again flowed into the tubule micro channel 12 and the water 400 is flowed through the tubule micro channel water inlet 32, electro osmotic flow occurs at the tubule micro channel water inlet 32 through which the water 400 containing no particles is flowed. Further, at a portion of the tubule micro channel 12 where the water 400 containing glucose 211 and the urea 212 which has been flowed through the waste passage 42 and the water 400 containing no particles which has been flowed through the water inlet 32 contact each other, the diffusion occurs similar to the glomerulus micro channel 11. Such electro osmotic flow and diffusion, among the glucose 211 and the urea 212 which are the small molecule 210, as shown in FIG. 3, most of the urea 212 remains to be discharged through the waste passage 42, and the glucose 211 moves to the newly flowed water 400 so as to be discharged through the blood passage 23. At this time, the blood 200 containing the hemoglobin 221 discharged from the glomerulus micro channel 11 may flow in the blood passage 23. Meanwhile, the water 400 containing the glucose 211 may flow in the separate blood passage 23, or may be merged with the blood 200 containing the hemoglobin 221.

Or, different from the case shown in FIG. 3, the newly flowed water 400 containing the glucose 211 may not be discharged directly through the blood passage 23 but may move through a separate passage different form the passage through which the water 400 containing the urea 212 is discharged among the waste passage 42. That is, the waste passage 42 may be doubly provided.

Subsequently, function and effect of the Henle's loop micro channel 13 will be described.

Figure 4:
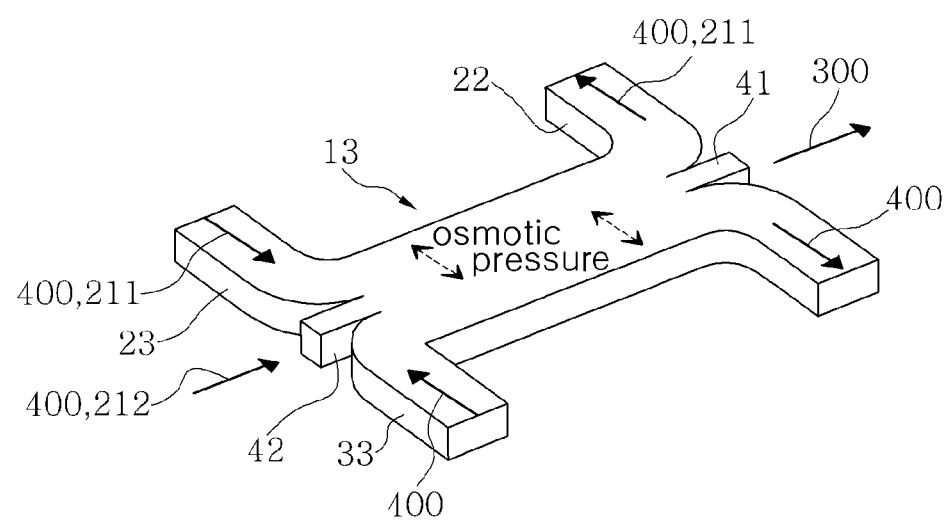
FIG. 4 is a conceptual diagram of a Henle's loop micro channel.

Referring to FIG. 1 and FIG. 4, the Henle's loop micro channel 13 regulates the amounts of water, according to the osmotic pressure, respectively in the water 400 containing the glucose 211, the water 400 containing the urea 212, and the water 400 which is flowed thereinto separately from the water 400 containing the glucose 211 and the water 400 containing the urea 212, and subsequently can merge the water 400 containing the glucose 211 into the blood 200 containing the remained hemoglobin 221 to discharge as the purified blood 200, and can discharge the water 400 containing the urea 212 as the water 400 containing the waste 300. Here, the osmotic pressure may be the pressure formed by a phenomenon that when two liquids with different concentrations are divided by a semipermeable membrane, the solvent moves from the side of lower concentration of the solute to the side of higher concentration of the solute.

Exemplarily, referring to FIG. 1 and FIG. 4, balance of concentration of the water 400 among the water 400 containing the glucose 211 flowed through the blood passage 23 and the water 400 containing the urea 212 flowed through the waste passage 42, and the water 400 without particles flowed through the Henle's loop micro passage water inlet 33 can be made, and at this time diffusion may occur together. Subsequently, the water 400 containing the glucose 211 in which the amount of water has been regulated may be merged with the blood 200 containing the hemoglobin 221 to be discharged through the blood outlet 22, and the water 400 containing the urea 212 in which the amount of water has been regulated may be discharged through the waste outlet 41 as the water 400 containing the waste 300, i.e., urine.

Here, the water 400 containing the glucose 211 may be merged with the blood 200 containing the hemoglobin 221 before flowing into the Henle's loop micro channel 13, as described above. In addition, as described above, the water 400 containing the glucose 211 may be flowed into the Henle's loop micro channel 13 through a passage separated from the waste passage 42 through which the water 400 containing the urea 212 among the waste passage 42 instead of the blood passage 23.

For reference, the artificial nephron device 100 may be formed approximately in a size of 2.0 cm of width, 1.0 cm of length, and 0.1 cm of height through micro machining process. In addition, the urea 212 in the blood 200 is not completely removed by the artificial nephron device according to an embodiment of the present invention, but the concentration of the urea 212 in the blood 200 can be reduced lower than 300 mM to simulate a real nephron of a human body. A real nephron of a human body can be simulated by achieving approximately 54 ml/min of the blood purification rate (clearance rate) in the test of function of a kidney. In addition, through the integration of a plurality of the artificial nephron devices according to an embodiment of the present invention, an artificial kidney of super high efficiency can be provided.

Figure 5:
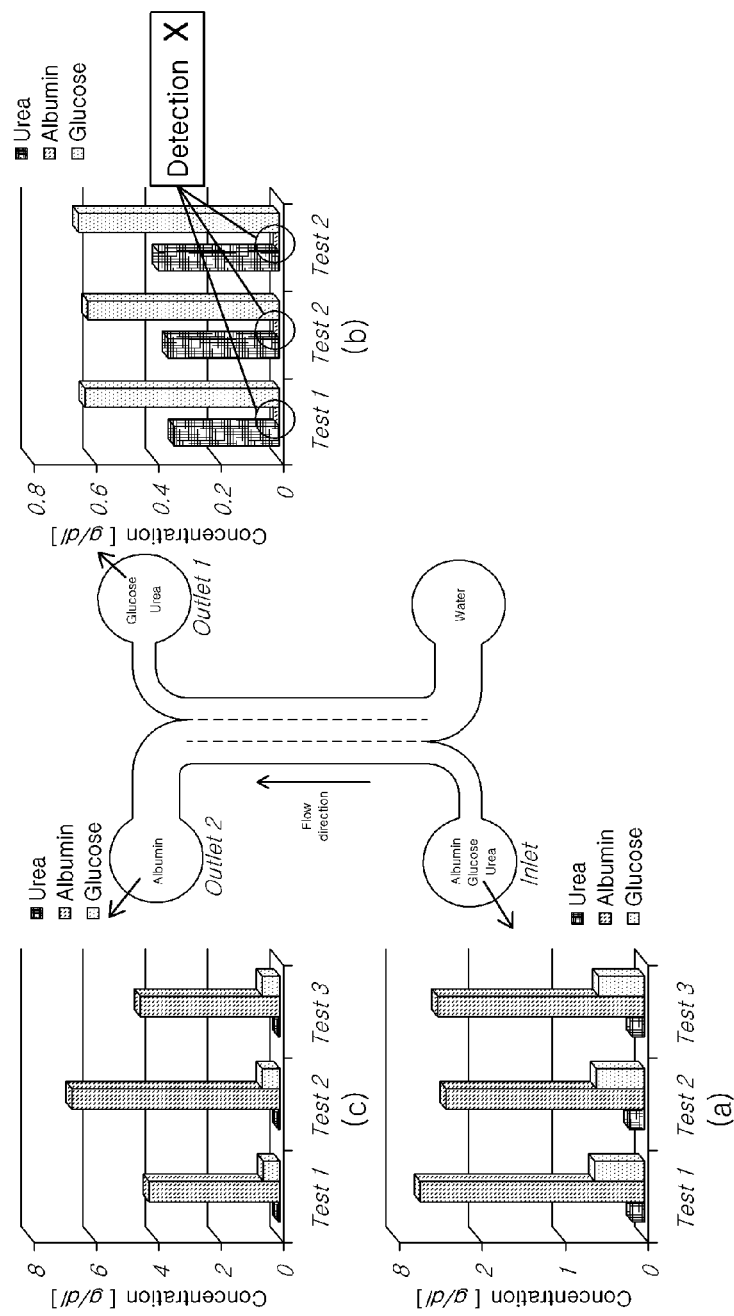
FIG. 5 is a graph showing change in concentration in experiment result of particle separation flow in a glomerulus micro channel observed by a hemodialyzer using an artificial nephron device according to an embodiment of the present invention.
Figure 6:
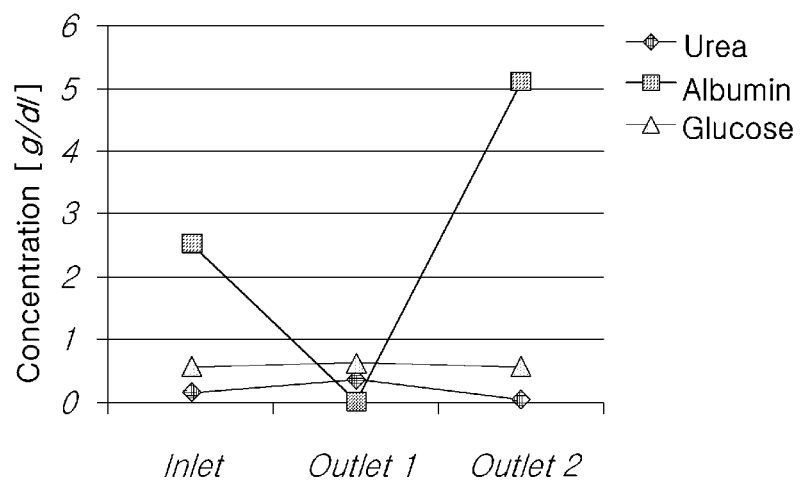
FIG. 6 is a graph showing change progress of the result of respective particles of a hemodialyzer at respective positions of glomerulus micro channel in the experiment result of particle separation flow in a glomerulus micro channel using artificial nephron device according to an embodiment of the present invention.

FIG. 5 is a graph showing change in concentration in experiment result of particle separation flow in a glomerulus micro channel observed by a hemodialyzer using an artificial nephron device according to an embodiment of the present invention, and FIG. 6 is a graph showing change progress of the result of respective particles of a hemodialyzer at respective positions of glomerulus micro channel in the experiment result of particle separation flow in a glomerulus micro channel using artificial nephron device according to an embodiment of the present invention.

Referring to FIG. 5 and FIG. 6, flow is introduced through an inlet and water is supplied at the opposite side, and the flow is discharged through an outlet 1 and an outlet 2. Referring to the graphs of FIG. 5 and FIG. 6 it can be seen that Albumin does not flow to the outlet 1 and the concentration of Albumin increases a little bit at the outlet 2. From this result, it can be known that the separation of Albumin from glucose and urea which is the function of the glomerulus micro channel is performed well.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. An artificial nephron device comprising:
  a multi micro channel in which while blood, which contains waste, and water are passing therethrough the waste is separated so as to purify the blood and the separated waste is concentrated into the water to be discharged, wherein the multi micro channel comprises a glomerulus micro channel configured to simulate a Glomerulus, a tubule micro channel configured to simulate a Tubule, and a Henle's loop micro channel configured to simulate a Henle's loop;
  a blood purification passage including a blood inlet through which the blood is supplied, a blood outlet through which the blood purified while passing through the multi micro channel is discharged, and a blood passage which sequentially connects the blood inlet, the glomerulus micro channel, the tubule micro channel, the Henle's loop micro channel and the blood outlet;
  a water inlet flowing water into the glomerulus micro channel, the tubule micro channel and the Henle's loop micro channel; and
  a waste concentration passage including a waste outlet through which the waste having been concentrated into the water while passing through the multi micro channel is discharged, and a waste passage which sequentially connects the glomerulus micro channel, the tubule micro channel, the Henle's loop micro channel and the waste outlet, wherein the glomerulus micro channel separates a small molecule from the blood and merges the small molecule into the water and allows a large molecule to remain in the blood, the large molecule comprises hemoglobin, and the small molecule comprises glucose and urea, wherein the tubule micro channel separates the water containing the small molecule into water containing the glucose and water containing the urea, and wherein the Henle's loop micro channel regulates amounts of water, according to osmotic pressure, respectively in the water containing the glucose, the water containing the urea, and water which is flowed thereinto separately from the water containing the glucose and the water containing the urea, and subsequently merges the water containing the glucose into the blood containing the remained hemoglobin to discharge as the purified blood, and discharges the water containing the urea as the water containing the waste.

2. The artificial nephron device of claim 1, wherein the glomerulus micro channel flows water thereinto and uses diffusion for the separation between the large molecule and the small molecule.

3. The artificial nephron device of claim 1, wherein the tubule micro channel flows water thereinto separately from the water containing the small molecule and uses diffusion and electro osmotic flow for the separation between the glucose and the urea.

4. The artificial nephron device of claim 1, wherein the water inlet flows water into the tubule micro channel separately from the water containing the small molecule and the tubule micro channel uses diffusion and electro osmotic flow for the separation between the glucose and the urea.

5. The artificial nephron device of claim 1, wherein the water inlet includes three separate water inlets, a first of the three separate water inlets supplies water into the glomerulus micro channel, a second of the three separate water inlets supplies water into the tubule micro channel and a third of the three separate water inlets supplies the water which is flowed into the Henle's loop micro channel separately from the water containing the glucose and the water containing the urea.

6. An artificial nephron device for purifying blood containing hemoglobin, glucose and urea, the artificial nephron device comprising:
   a multi micro channel having the blood and water pass therethrough, the urea being separated from the blood in the multi micro channel so as to purify the blood into purified blood, the separated urea being concentrated into the water, the multi micro channel including
      a glomerulus micro channel configured to simulate a Glomerulus, the glomerulus micro channel separating the glucose and the urea from the blood and merging the glucose and the urea into the water, the glomerulus micro channel allowing the hemoglobin to remain in the blood,
      a tubule micro channel configured to simulate a Tubule, the tubule micro channel separating the water containing the glucose and the urea into water containing the glucose and water containing the urea, and
      a Henle's loop micro channel configured to simulate a Henle's loop, the Henle's loop micro channel regulating amounts of water, according to osmotic pressures between the water containing the glucose, the water containing the urea, and water which is flowed into the Henle's loop micro channel separately from the water containing the glucose and the water containing the urea, the Henle's loop micro channel subsequently forming the purified blood by merging the water containing the glucose into the blood containing the hemoglobin, the Henle's loop micro channel discharging the purified blood, the Henle's loop micro channel further discharging the water containing the urea as waste;
   a blood purification passage including
      a blood inlet through which the blood is supplied,
      a blood outlet through which the purified blood is discharged, and
      a blood passage connecting the blood inlet, the glomerulus micro channel, the tubule micro channel, the Henle's loop micro channel and the blood outlet in that stated order;
   a water inlet flowing water into each of the glomerulus micro channel, the tubule micro channel and the Henle's loop micro channel; and
   a waste concentration passage including
      a waste outlet through which the waste is discharged, and
      a waste passage which connects the glomerulus micro channel, the tubule micro channel, the Henle's loop micro channel and the waste outlet in that stated order.

7. The artificial nephron device of claim 6, wherein the water inlet includes three separate water inlets, a first of the three separate water inlets supplies water into the glomerulus micro channel, a second of the three separate water inlets supplies water into the tubule micro channel and a third of the three separate water inlets supplies the water which is flowed into the Henle's loop micro channel separately from the water containing the glucose and the water containing the urea.

* * * * *